US008622940B2

(12) United States Patent
Udassi et al.

(10) Patent No.: US 8,622,940 B2
(45) Date of Patent: Jan. 7, 2014

(54) DEVICE FOR ASSISTING CARDIAC PULMONARY RESUSCITATION (75) Inventors: Jai P. Udassi, Gainesville, FL (US); Arno L. Zaritsky, Norfolk, VA (US); Ikram Haque, Houston, TX (US); Sharda Udassi, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 437 days.

(21) Appl. No.: 12/810,922

(22) PCT Filed: Jan. 2, 2009

(86) PCT No.: PCT/US2009/030023
§ 371 (c)(1),
(2), (4) Date: Dec. 1, 2010

(87) PCT Pub. No.: WO2009/089096
PCT Pub. Date: Jul. 16, 2009

(65) Prior Publication Data
US 2011/0066089 A1    Mar. 17, 2011

Related U.S. Application Data (60) Provisional application No. 61/018,565, filed on Jan. 2, 2008.

(51) Int. Cl.
A61H 31/00    (2006.01)
(52) U.S. Cl.
USPC .................................... 601/41; 601/1; 2/159
(58) Field of Classification Search
USPC ........... 601/41, 43, 44, 6, 9, 10, 11, 148–151, 601/134–135; 2/158, 159, 161.3, 160, 163, 2/910, 917, 161.8
See application file for complete search history.

(56) References Cited

U.S. PATENT DOCUMENTS

| | | | | |
|---|---|---|---|---|
| 4,077,400 A | * | 3/1978 | Harrigan | 601/1 |
| 4,689,828 A | * | 9/1987 | Brewer | 2/21 |
| 4,747,397 A | * | 5/1988 | Magovern | 601/135 |
| 4,809,683 A | * | 3/1989 | Hanson | 601/41 |
| 5,454,779 A | | 10/1995 | Lurie et al. | |
| 5,487,722 A | * | 1/1996 | Weaver et al. | 601/41 |
| 5,517,692 A | * | 5/1996 | Wunderlich-Kehm | 2/21 |
| 5,636,406 A | * | 6/1997 | Strong | 15/227 |
| 5,770,297 A | * | 6/1998 | Grubich | 428/99 |
| 6,587,726 B2 | | 7/2003 | Lurie et al. | |
| 7,361,151 B2 | * | 4/2008 | Wood | 601/41 |
| 2001/0001883 A1 | * | 5/2001 | Wanzenried | 2/21 |
| 2005/0013957 A1 | | 1/2005 | Leschinsky | |

OTHER PUBLICATIONS

Bethanie Christopher, "The ABC & 1-2-3 (D) of CPR" [online] Mar. 2007 [retrieved Apr. 30, 2009] retrieved from internet http:www.lifesavered.com/BLSStudyGuide.pdf>infant row.

* cited by examiner

Primary Examiner — Justine R Yu
Assistant Examiner — Michael Tsai
(74) Attorney, Agent, or Firm — Timothy H. Van Dyke; Beusse, Wolter, Sanks, Mora & Maire, P.A.

(57) ABSTRACT

Embodiments provided herein include CPR assisting devices. Certain embodiments pertain to a device that may be adhered to patient's chest to aid in active compression/decompression CPR. The device may be incorporated with the AED pad for implementation in conjunction with defibrillator machine.

3 Claims, 6 Drawing Sheets

DEVICE FOR ASSISTING CARDIAC PULMONARY RESUSCITATION

CROSS REFERENCE TO RELATED APPLICATIONS

This application is a U.S. national stage filing of PCT/US09/30023 filed Jan. 2, 2009, which claims the benefit of U.S. Ser. No. 61/018,565 filed Jan. 2, 2008, all of which are incorporated herein in their entireties.

BACKGROUND

Cardiopulmonary resuscitation (CPR) is a well known and valuable method of first aid. CPR is used to resuscitate people who have suffered from cardiac arrest after heart attack, electric shock, chest injury and many other causes. During cardiac arrest, the heart stops pumping blood, and a person suffering cardiac arrest will soon suffer brain damage from lack of blood supply to the brain. Thus, CPR requires repetitive chest compression to squeeze the heart and the thoracic cavity to pump blood through the body. Very often, the victim is not breathing, and mouth to mouth artificial respiration or a bag valve mask is used to supply air to the lungs while the chest compression pumps blood through the body. The methods of providing oxygenated airflow to the lungs and getting rid of Co2 are referred to as oxygenation and ventilation respectively.

It has been widely noted that CPR and chest compression can save cardiac arrest victims, especially when applied immediately after cardiac arrest. Chest compression requires that the person providing chest compression repetitively push down on the sternum of the victim at 100 compressions per minute. CPR and closed chest compression can be used anywhere, wherever the cardiac arrest victim is stricken. In the field, away from the hospital, CPR may be accomplished by ill-trained by-standers or highly trained paramedics and ambulance personnel. The conventional thinking is that The victim's chest is compressed by the rescuer, ideally at a rate and depth of compression in accordance with medical guidelines, e.g., the American Heart Association (AHA) guidelines.

Traditional CPR is performed by active compression of the chest by direct application of an external pressure to the chest. This phase of CPR is typically referred to as the compression phase. After active compression, the chest is allowed to expand by its natural elasticity which causes expansion of the patient's chest wall. This phase is often referred to as the relaxation or decompression phase. Such expansion of the chest allows some blood to enter the cardiac chambers of the heart. The procedure as described, however, is inefficient to oxygenate the body. Consequently, conventional CPR also requires periodic ventilation of the patient. This is commonly accomplished by a mouth to-mouth technique or by using positive pressure devices, such as a self-inflating bag which delivers air through a mask, an endotracheal tube, or other artificial airway.

In order to increase cardiopulmonary circulation induced by chest compression, a technique referred to as active compression-decompression (ACD) has been developed. According to ACD techniques, the active compression phase of traditional CPR is enhanced by pressing an applicator body against the patient's chest to compress the chest. Such an applicator body is able to distribute an applied force substantially evenly over a portion of the patient's chest. More importantly, however, the applicator body is sealed against the patient's chest so that it may be lifted up to 10% beyond the neutral position to actively expand the patient's chest during the relaxation or decompression phase. The resultant negative intrathoracic pressure induces venous blood to flow into the heart from the peripheral venous vasculature of the patient resulting in better cardiac out put in subsequent compression. Devices and methods for performing ACD to the patient are described in U.S. Pat. Nos. 5,454, 779 and 5,645,552, the complete disclosures of which are herein incorporated by reference.

CPR is often administered in conjunction with other procedures which, taken together, are referred to as advanced cardiac life support (ACLS) for adults and pediatric advance life support (PALS) for children. Most commonly, CPR is administered while the patient undergoes both electrocardiographic monitoring (ECM) and electrical defibrillation. Both ECM and defibrillation require the attachment of electrodes to the patient's chest. The inventors have recognized that the need to attach electrodes can interfere with the ability to administer CPR, particularly the ability to administer manual CPR and give shock to the patient at the same time.

SUMMARY

While devices are available to perform ACD are available, the inventors have recognized certain problems and shortcomings of current devices. The subject invention is based on the inventors' work toward improving ACD devices. Current ACD devices such as that describe in U.S. Pat. No. 5,645,522 and European Patent Pub. 0623334 are hard rigid devices that incorporate a metal suction cup. The suction cup is pressed against a patient's chest and engages to the chest via a vacuum. However, the inventors have realized that such conventional ACD devices apply an inordinate amount of pressure around the periphery of the suction cup. This often leads to undesired tissue damage and lacerations to the chest. Further, due to the rigidity of the device and the pressure applied during CPR, application of such device can and often does fracture the patient's ribs. In one embodiment of the subject invention, the invention pertains to an apparel device such as a glove or mitten designed to be worn on the hands of a medical assistance provider. The apparel device is made of a flexible, soft material and includes a pad located adjacent to the palm area. The pad is engaged to a patient's chest via an adhering material. The adhering material may be an adhesive such as a suitable glue that is preapplied to the pad and covered. Before use, the cover is removed and the pad is pressed upon the patient's chest. Alternatively, adhering material is applied to the pad immediately prior to application of the pad to the patient's chest. In a specific embodiment, the pad may comprise a cover layer, an adhesive layer subjacent to the cover layer, a first a hook and loop layer (e.g. Velcro) subjacent to the adhesive layer, second hook and loop layer subjacent to the first hook and loop layer. The pad is secured to an apparel device body made up of a flexible material. The pad may be secured to the body via an adhesive, sewing, melding, etc. The apparel device will allow a medical assistance provider to easily put on their hand and properly position on a patient's chest and apply ACD while minimizing undesired tissue damage to the patient. Furthermore the implementation of an apparel device for administering ACD is much easier as compared to conventional devices. Utilizing embodiments of the invention leads to significantly longer endurance for sustaining CPR, as well as sustaining highly effective CPR.

The inventors have recognized that current ACD devices are not tailored for administering CPR to infants and small children. In one embodiment, the invention pertains to a device designed for placement on a user's thumbs. The device comprises a first and second body portion that surrounds the thumbs with a pad disposed on each. The pad is designed to adhere to the chest of an infant patient. This embodiment will assist with applying not only CPR on an infant but, more importantly, to apply infant ACD. The user will apply pressure to the patient's chest with their thumbs and pull back with their thumbs. As the user pulls back, the device will pull up and decompress the patient's chest.

As discussed above, CPR is often administered in conjunction with other procedures such as electrocardiographic monitoring (ECM) and electrical defibrillation. Both ECM and defibrillation require the attachment of electrodes to the patient's chest. The inventors have recognized a shortcoming with conventional ACLS strategies and devices in that they require suspension of CPR during a defibrillation event. Defibrillation involves the application and a high voltage electric shock to the thoracic cavity of the patient in an attempt to reset the heart and normalize heart rate. Consequently, medical assistance personnel must suspend the CPR while defibrillation occurs so as to avoid electric shock. This results in a stoppage of CPR for several seconds in a setting where any pause in CPR dramatically decreases the chances of a successful outcome. Accordingly, another embodiment of the invention pertains to an apparel device that includes a pad for adhering to a patient's chest and an electrically insulating layer that allows a medical assistance provider to maintain wear of the apparel device engaged to the patient even upon application of electric shock to patient.

According to another embodiment, the apparel device is adapted as an AED pad or to co-function as an AED pad with the defibrillation machine. The embodiment includes an apparel body for fitting over the user's hand which is connected to or integrated with a pad that includes an electrode. An insulating layer is included between the electrode and the apparel device so as to prevent electric shock to the medical assistance provider.

Figure 11:
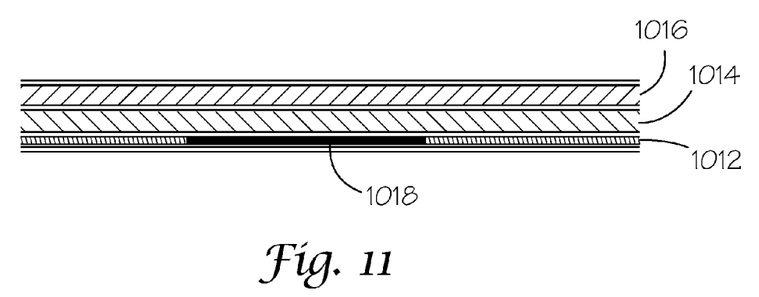
FIG. 11 shows a cross-section of a portion of an ACD apparel device embodiment.

In another embodiment, the invention pertains to a defibrillation harness such as that shown in FIG. 11 which has an apparel device described herein attached to the center bridge portion. The harness is situated on the patient and the medical assistance provider positions their hand in the apparel device. CPR and defibrillation can be administered to the patient in an efficient and minimally damaging manner. Further, the bridge can be insulated or otherwise avoid the delivery of shock thereby allowing the administration of CPR with minimal interruption.

DETAILED DESCRIPTION

Figure 1:
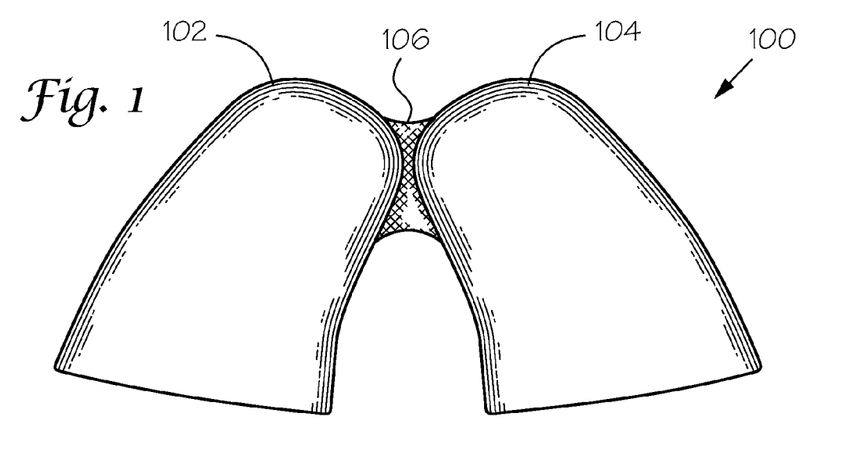
FIG. 1 shows a side-view image of an ACD device embodiment designed for infants and small children.
Figure 2:
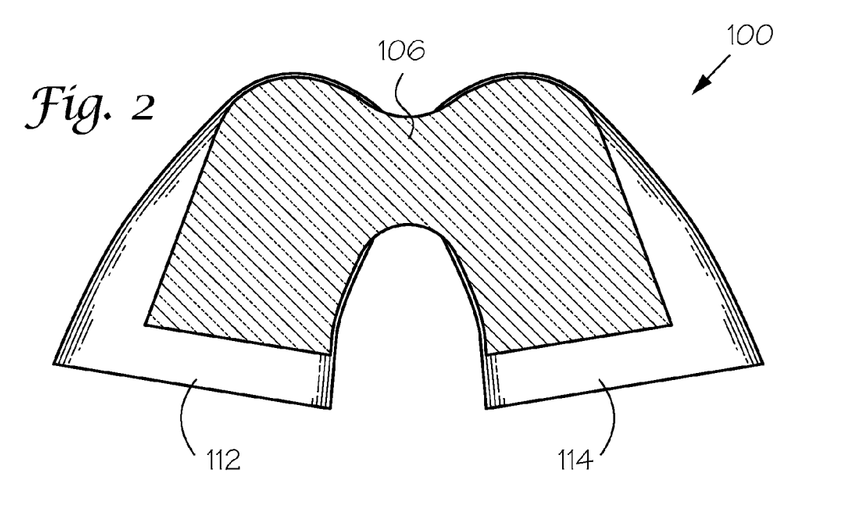
FIG. 2 shows a side-view image of the embodiment shown in FIG. 1 on its opposite side.

Turning to FIG. 1-2, what is shown is first and second a side-view images of an ACD apparel device embodiment 100 of the present invention. The apparel device 100 is specifically tailored for administration of ACD to infants and small children. The device 100 includes a first and second thumb holder 102, 104 connected together and an adhering pad 106. The user inserts their thumbs into openings 112 and 114. The device 100 is adhered to a patient's chest via the adhering pad 106. ACD is applied by applying pressure to the patients chest and pulling back on the chest using the medical assistance provider's thumbs.

Figure 3:
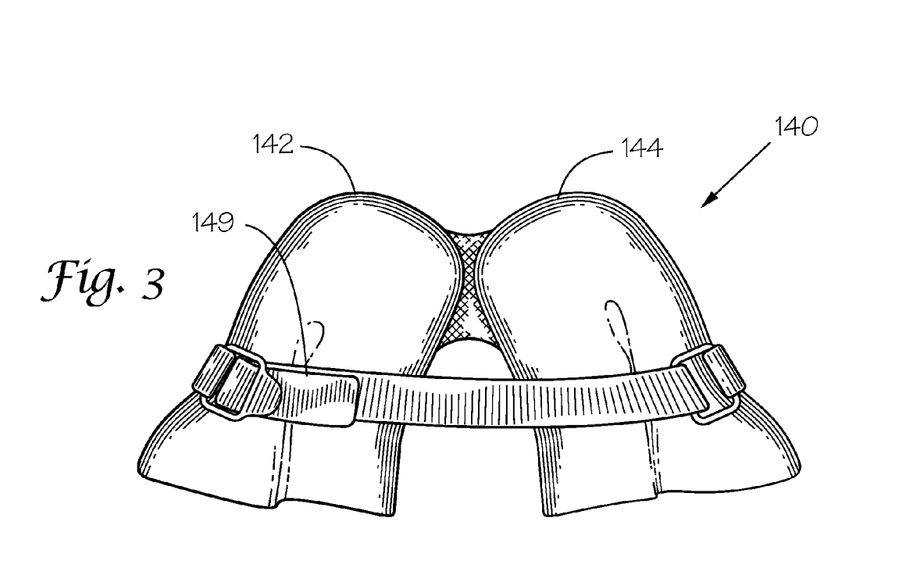
FIG. 3 shows a side-view image of another embodiment designed for ACD administration to infants and small children.
Figure 8:
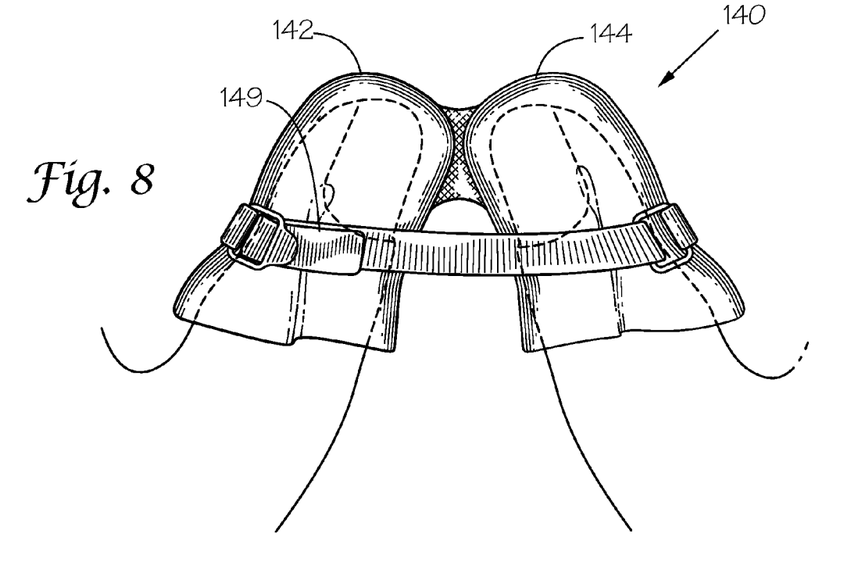
FIG. 8 shows a side view perspective image of the embodiment shown in FIG. 3 with a user's thumbs placed therein.

An alternative apparel device embodiment 140 is shown in FIG. 3. This embodiment 140 includes a strap 149 that surround thumbholder lobes 142, 144 to provide additional support. Both embodiments 100 and 140 are made of a soft flexible material, such as a woven or non-woven fabric, leather, vinyl, flexible plastic, rubber, and the like, or combinations thereof. FIG. 8 shows a user's thumbs positioned with the embodiment 140.

Figure 4:
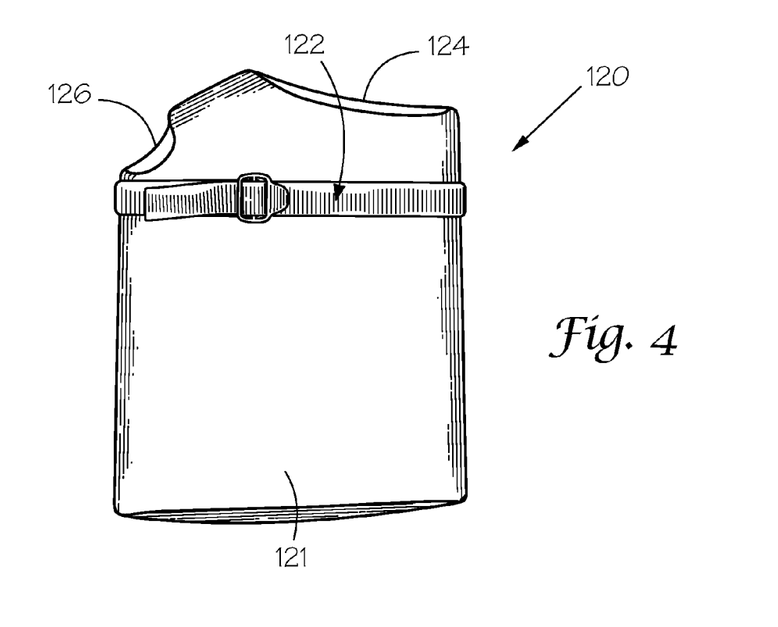
FIG. 4 shows a side view image of an ACD device embodiment designed for administration of ACD to adults.
Figure 5:
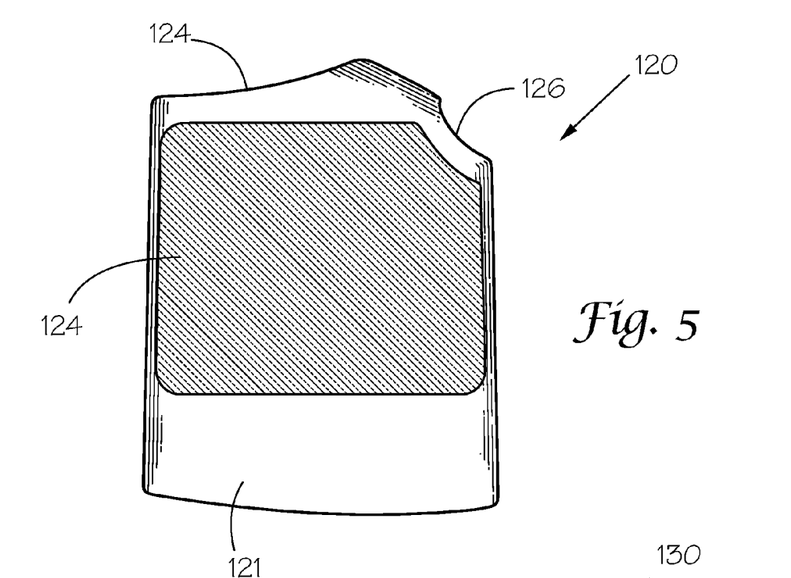
FIG. 5 shows a side view image of the embodiment shown in FIG. 4 on its opposite side.
Figure 9:
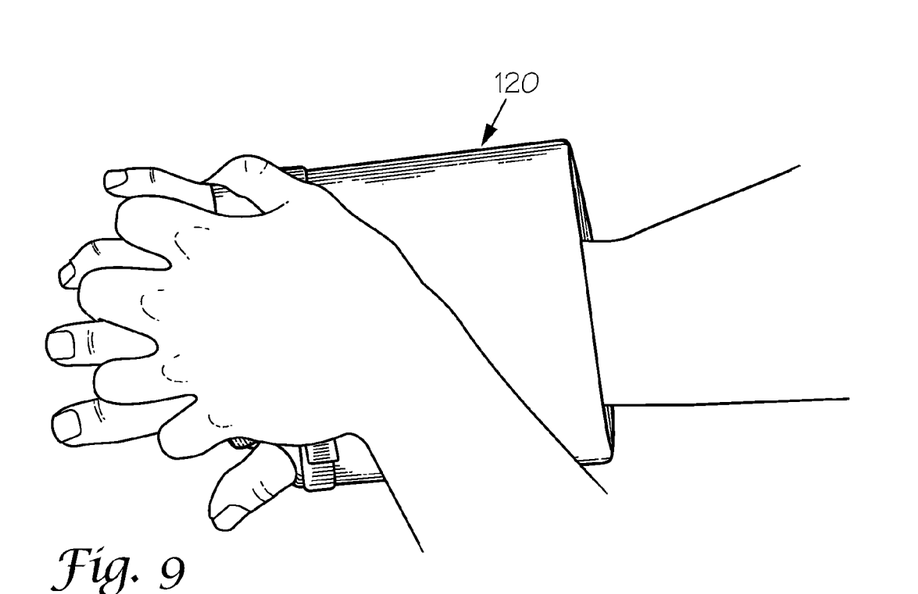
FIG. 9 shows a side perspective image of the embodiment shown FIGS. 4 and 5 with a users hand positioned therein.

FIG. 4 shows another apparel device embodiment 120 designed for administering ACD to adults. The embodiment 120 is made of a fabric and is configured as a mitten body 121. The embodiment 120 comprises an aperture 124 and an aperture 126 for extending a user's fingers and thumb, respectively, through the apparel device 120. The fingers could be enclosed, but the apertures facilitate interlocking of the user's hands. FIG. 9 shows a users hand positioned with the glove embodiment 120. The embodiment 120 also includes an adhering pad 124 that adheres to a patient's chest. The embodiment 120 also comprises an adjustable strap that support's the embodiment at the top portion of the user's inserted hand.

Figure 6:
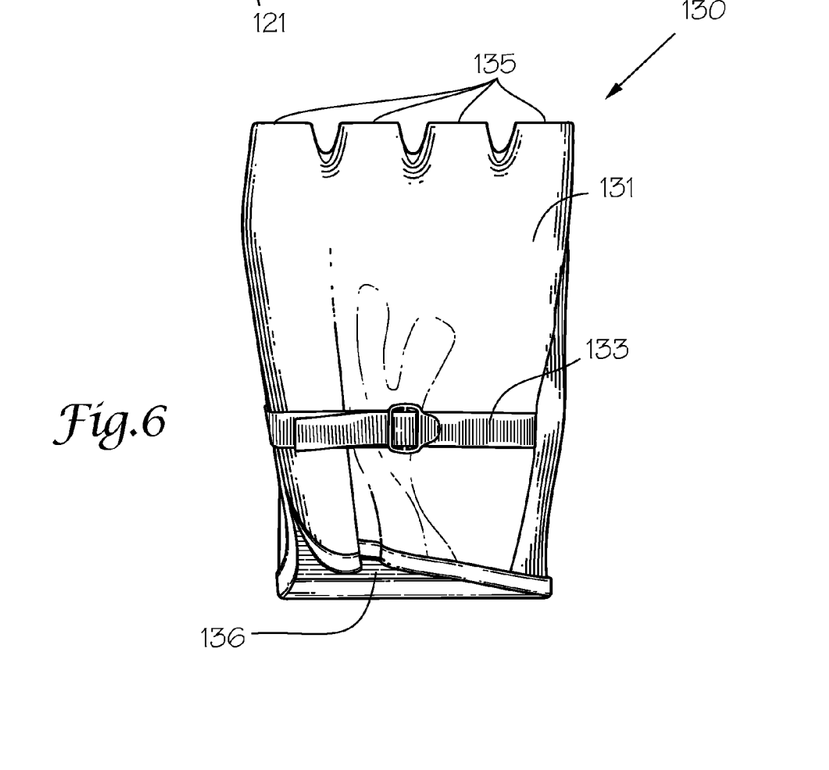
FIG. 6 shows a side view image of an ACD device embodiment designed for administration of ACD to adults.
Figure 7:
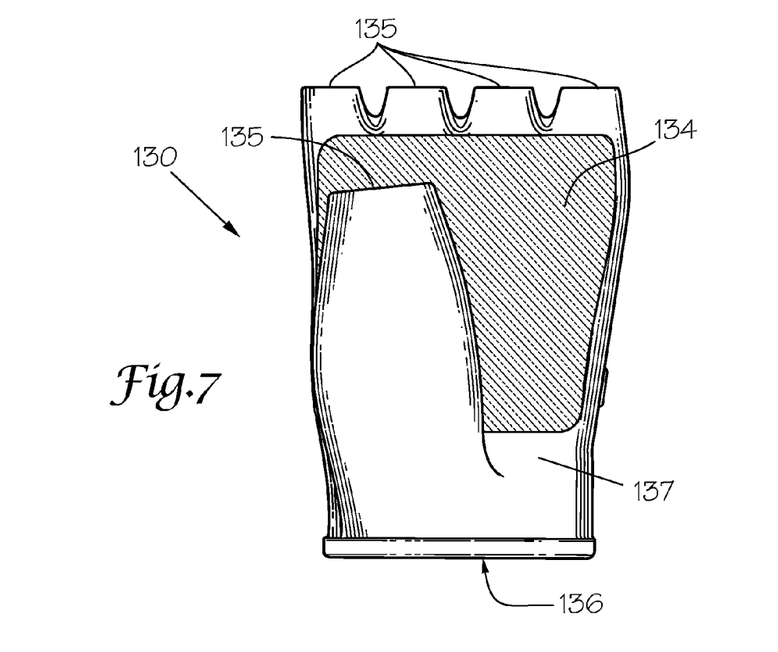
FIG. 7 shows a side view image of the embodiment shown in FIG. 6.

FIG. 6 shows an alternative apparel device embodiment 130 configured as an open-ended glove 131. A user inserts their hand through opening 136 and extends their fingers through openings 135. Similar to the glove type embodiment, the fingers can be covered, but allowing exposure of the fingers assists in the optimal interlocking of the user's hands. The opening for the thumb is hidden. FIG. 7 shows the palm side 137 of the embodiment 130. Connected to or integrated with the palm side 137 is an adhering pad 134. The adhering pad 134 is adhered to a patient's chest prior to administration of ACD.

Though a pad layer of the above described embodiments provides a surface area for adhering the embodiment to the patient's chest, the inventors note that an adhering material could be applied directly on the fabric of the apparel body or thumbholder.

Figure 10:
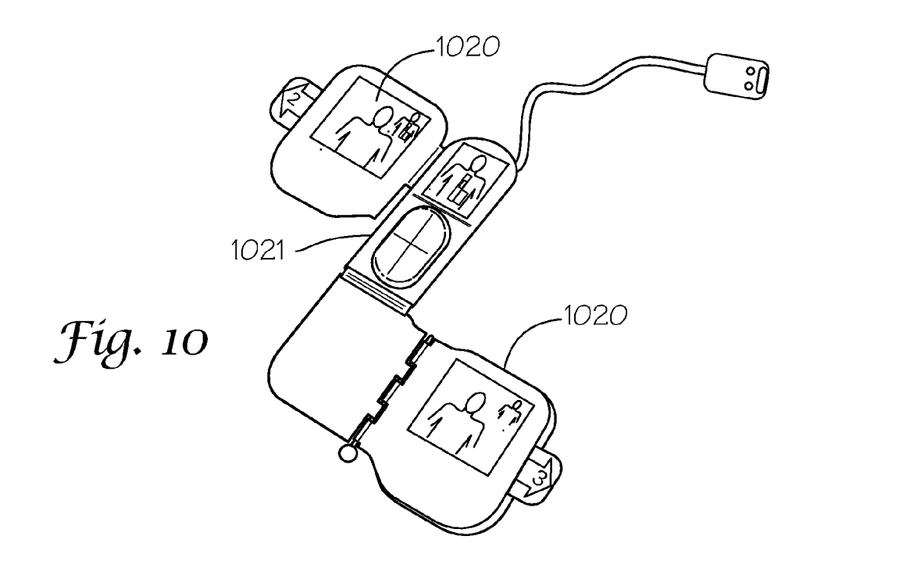
FIG. 10 shows an image of a convention AED harness.

FIG. 10 shows a commercially available defibrillating harness comprising pads 1020 and bridge portion 1021. The bridge portion 1021 can be adapted to include an apparel device for ACD. The bridge 1021 may be insulated to allow application of electrical current to the pads 1020 without shocking the medical assistance provider.

Figure 12:
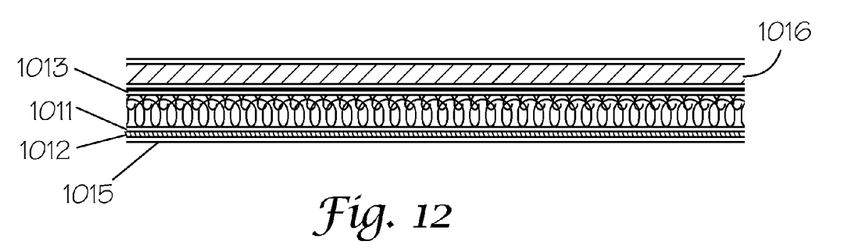
FIG. 12 shows a cross-section of a portion of an embodiment of an apparel device.

FIG. 11 shows a cross section of a portion of an insulated apparel device embodiment. According to this embodiment, the apparel device comprises an adhesive pad 1012 with an electrode 1018 embedded therein for monitoring or applying electric shock. An apparel material layer 1016 and an insulating layer 1014. Alternatively the insulating layer is inside the apparel material layer. FIG. 12 shows a cross section of a portion of an embodiment of an apparel device designed for administering ACD to adults shown, wherein the apparel material layer 1016 is shown, and a cover layer 1015 is provided. An adhesive layer 1012 is subjacent to the cover layer 1015, a first hook and loop layer 1011 subjacent to the adhesive layer 1012 and a second hook and loop layer 1013 subjacent to the first hook and loop layer 1011.

EXAMPLE 1

Introduction: AHA 2005 guidelines emphasize complete relaxation during CPR since incomplete chest wall recoil during the decompression phase impedes venous return and decreases mean arterial, coronary and cerebral perfusion pressures. In animals ACD-CPR improves hemodynamics compared with standard CPR (S-CPR). We used a novel, simple and inexpensive Adhesive Glove Device to perform ACD-CPR in a manikin model.

Hypothesis: We hypothesized that ACD-CPR using an Adhesive Glove Device provides better chest decompression compare to S-CPR.

Methods: Laerdal™ Resusci Anne (Adolescent) manikin was modified to digitally record compression pressure(CP), compression depth(CD) and decompression depth (DD). Adhesive Glove Device consisted of an oven mitt modified to expose the fingers and thumb allowing interlocking of the fingers and an adjustable strap for proper fit. A wide Velcro patch was sewn to the palmer aspect of the glove and the counter Velcro patch was glued to an adhesive pad applied to the manikin chest wall. BLS or PALS-certified healthcare providers were prospectively randomized to perform either standard CPR or AGD-ACD-CPR for 5 minutes with 30:2 compression: ventilation ratio using crossover design. During AGD-ACD-CPR subjects were asked to actively pull up during decompression. Subjects were blinded to data recordings. Data (mean±SEM) was analyzed using 2 sided paired t-test; alpha $\leq 0.05$ was considered significant.

Results: None of the 16 subjects using S-CPR achieved complete decompression to baseline. Chest decompression was greater with AGD-ACD-CPR; the mean decompression difference was 0.07±0.02 inches, p=0.003. Despite instructions to pull up, only 50% of AGD group decompressed to or beyond baseline. There was no difference between techniques in CD or CP.

Conclusions: Most rescuers don't achieve complete chest recoil during standard CPR, which may be achieved with use of our simple, inexpensive device.

EXAMPLE 2

Rescuer fatigue during Adhesive Glove Device-Active Compression Decompression-CPR (AGD-CPR).

Introduction: ACD-CPR improves homodynamic compared with standard CPR(S-CPR) in animals, but requires more work. In one study most participants felt that the ACD device was very difficult to use.

Hypothesis: ACD-CPR using our Adhesive Glove device in a manikin model results in more rescuer fatigue.

Methods: Laerdal™ Adolescent manikin was used. Adhesive glove device was a modified oven mitt exposing the fingers and thumb to allow interlocking of fingers and an adjustable strap for proper fit. A wide Velcro patch was sewn on the glove's palmer aspect and a counter Velcro patch was fixed to an adhesive pad applied to chest wall. Health care providers were randomized to perform either S-CPR or AGD-CPR for 5 minutes with 30:2 compression: ventilation ratio using crossover design. AGD-CPR subjects were told to actively pull during decompression. Rescuer heart rate(HR) and respiratory rate(RR) were recorded continuously along with recovery time(RT) for HR/RR to return to baseline and actual compressions delivered per minute. Rescuers reported subjective fatigue using a Likert Scale. Subjects were blinded to data recordings. Data(mean±SD) was analyzed using t-test; $p \leq 0.05$ was considered significant.

Results: In 16 subjects, HR at 5 minutes was 134±27 versus 131±23 (S-CPR v AGD-CPR; p=0.21). Similarly, RR at 5 minutes was 28±9 versus 28±6, p=0.34 & RT was 248 ±131 sec versus 316±165 sec with AGD-CPR, p=0.23. Compressions per minute were 90±20 versus 82±22 with AGD-CPR, p=0.02. There was no change in decompression depth over time in either group and no significant difference in subjective estimate of time when it became very difficult to continue CPR because of fatigue.

Conclusions: This study suggests that ACD-CPR using our simple inexpensive device does not result in excessive rescuer fatigue. Fewer actual compressions were given during ACD-CPR, probably because it takes longer to perform decompression. The clinical significance of 8 less compressions per minute needs to be determined.

EXAMPLE 3

Improved Chest Recoil Using a Novel Device for Active Chest Decompressions in Child Manikin CPR.

Introduction: Current CPR guidelines emphasize complete chest recoil. Incomplete chest recoil impedes venous return and thus cardiac output. In animals active compression-decompression CPR (ACD-CPR) improves hemodynamics compared with standard CPR (S-CPR). We developed a novel, simple, inexpensive Adhesive Glove Device (AGD) to perform ACD-CPR.

Hypothesis: It was hypothesized that ACD-CPR using an AGD provides better chest decompression compared to S-CPR in a child manikin without increased rescuer fatigue.

Methods: Laerdal™ Resusci Junior manikin was modified to digitally record compression pressure(CP), compression depth(CD) and decompression depth(DD). AGD consisted of a modified oven mitt exposing the fingers and thumb allowing interlocking. A wide Velcro patch was sewn to the palmer aspect and the counter Velcro patch was glued to the manikin chest wall. Certified healthcare providers (16/group) were prospectively randomized to perform either S-CPR or AGD-ACD-CPR for 5 minutes with 30:2 C:V ratio using crossover design with both one hand(OH) and two hand(TH) techniques. AGD subjects were asked to actively pull up during decompression. Subjects were blinded to data recordings. Rescuer heart rate(HR), respiratory rate(RR), recovery time (RT) and actual compressions delivered per minute were recorded. Data (mean±SEM) was analyzed using 2 sided paired t-test; p-value $\leq 0.05$ was considered significant.

Results: Chest decompression was greater with AGD-ACD-CPR; the mean decompression difference was 0.098±0.02 inches, p=<0.001 in OH and 0.099±0.02 inches, p=<0.001 in TH. Compressions delivered per minute were 85±22 (S-CPR) vs.74±23 (AGD-CPR), p=0.02 in OH group and 92±23 vs. 79±22, p=0.003 in TH. Among AGD-ACD-CPR groups, 56% of subjects in OH and 38% in TH decompressed to or beyond baseline. In S-CPR group, only 12% of subjects in OH and 18% in TH achieved complete chest recoil. No significant difference was observed in CD, CP, HR, RR and RT between the groups.

Conclusions: Use of the easy to use and inexpensive AGD resulted in improved chest decompression with out excessive rescuer fatigue. Most rescuers did not achieve complete chest recoil during standard CPR.

EXAMPLE 4

Active Compression Decompression-CPR in an Infant Manikin Model Using a Novel Adhesive Glove Device.

Introduction: In animals Active Compression-Decompression(ACD)-CPR improves hemodynamics compared with standard CPR (S-CPR). We evaluated the feasibility of achieving ACD-CPR with a novel, simple and inexpensive Adhesive Glove Device(AGD) in an infant manikin model using two thumb(TT) chest compression.

Hypothesis: AGD-ACD CPR provides better chest decompression compared to S-CPR in an infant manikin model without excessive rescuer fatigue.

Methods: Laerdal™ Baby ALS Trainer manikin was modified to digitally record compression pressure(CP), compression depth(CD) and decompression depth(DD). The thumb portion of two oven mitts were sewn together and a Velcro adhesive patch was stitched on the underside with an encircling adjustable strap for proper fit to create the AGD. An interlocking Velcro patch was glued to the manikin chest wall. Sixteen BLS or PALS certified healthcare providers were prospectively randomized to perform either two-thumb S-CPR or AGD-ACD-CPR for 5 minutes with a 30:2 compression:ventilation ratio using a crossover design. During AGD-ACD-CPR subjects were asked to pull up during chest decompression. Rescuer heart rate (HR), respiratory rate (RR), recovery time (RT) for HR/RR to return to baseline and actual compressions delivered per minute were recorded. Subjects were blinded to data recordings. Data (mean±SEM) was analyzed using 2 sided paired t-test; p-value ≤0.05 was considered significant Results: Chest decompression was greater with AGD-ACD-CPR; the mean DD difference was 0.11±0.02 inches, p=<0.001. Compressions given per minute were 102±21 in S-CPR group vs. 96±16 in AGD-ACD-CPR group, p=0.04. In AGD-CPR 75% and in S-CPR only 12% of subjects achieved complete recoil to or beyond baseline. There was no significant difference in CD, CP, HR, RR and RT between the groups.

Conclusions: Active decompression and improved recoil was achievable with the use of our simple, inexpensive AGD in this infant CPR model. Use of our device did not result in excessive rescuer fatigue compared to S-CPR. The clinical significance of 6 less compressions/minute in the AGD-CPR group needs to be determined.

The disclosures of all cited patent documents, publications and references are incorporated herein in their entirety to the extent not inconsistent with the teachings herein. It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A device for administering active compression-decompression to an infant comprising a first sleeve configured for placement over a medical assistance provider's first thumb and a second sleeve for placement over a medical assistance provider's second thumb, said first an' second sleeves being coupled to each other and a pad disposed on each of said first and second sleeves, said pad comprising an adhering material.

2. A device for administering active compression-decompression to an infant comprising a first sleeve configured for placement over and to surround a medical assistance provider's first thumb and a second sleeve for placement over and to surround a medical assistance provider's second thumb, said first and second sleeves each being coupled with at least one pad comprising adhering material, wherein said first and second sleeves are associated with a common pad or a different pad, and wherein said pad comprises an adhering material.

3. A method for applying active compression-decompression to an infant comprising:
    obtaining a device comprising a first sleeve configured for placement over a medical assistance provider's first thumb and a second sleeve for placement over a medical assistance provider's second thumb, said first and second sleeves each being associated with at least one pad comprising an adhering material, wherein said first and second sleeves are coupled with a common pad or a different pad;
    inserting said first and second thumbs into first and second sleeves, respectively;
    adhering said device to an infant's chest in need of compression-decompression; and
    using said device to apply active compression-decompression.

* * * * *